United States Patent [19]

Cosentino et al.

[11] 4,417,888
[45] Nov. 29, 1983

[54] PERCUTANEOUS IMPLANT

[75] Inventors: Louis C. Cosentino, Wayzata; Felix J. Martinez, Plymouth, both of Minn.

[73] Assignee: Renal Systems, Inc., Minneapolis, Minn.

[21] Appl. No.: 358,229

[22] Filed: Mar. 15, 1982

[51] Int. Cl.³ .......................... A61M 5/00; A61F 1/00
[52] U.S. Cl. .................................. 604/175; 128/1 R; 604/29
[58] Field of Search ............... 128/213 A, 214 R, 348, 128/9.2 D, 247, DIG. 26, 350 R, 334, 1 R; 3/1; 604/27–29, 174, 175, 280, 283, 30, 32–34; 428/311

[56] References Cited

U.S. PATENT DOCUMENTS

| 3,402,710 | 9/1968 | Paleschuck . | |
|---|---|---|---|
| 3,643,658 | 2/1972 | Steinemenan | 128/92 D |
| 3,663,965 | 5/1972 | Lee et al. . | |
| 3,707,967 | 1/1973 | Kitrilakis et al. | 604/175 X |
| 3,765,032 | 10/1973 | Palma . | |
| 3,783,868 | 1/1974 | Bokros . | |
| 4,015,601 | 4/1977 | Bokros et al. . | |
| 4,016,884 | 4/1977 | Kwan-Gett | 128/DIG. 26 |
| 4,073,999 | 2/1978 | Bryan et al. | 3/1 X |
| 4,092,983 | 6/1978 | Slivenko . | |
| 4,108,173 | 8/1978 | Slivenko et al. . | |
| 4,108,174 | 8/1978 | Slivenko et al. . | |
| 4,164,221 | 8/1979 | Bentley et al. . | |
| 4,184,497 | 1/1980 | Kolff et al. | 604/29 X |
| 4,278,092 | 7/1981 | Borsanyi et al. | 604/29 X |
| 4,306,545 | 12/1981 | Ivan et al. | 128/1 R |
| 4,306,976 | 12/1981 | Bazzato | 604/29 X |
| 4,318,401 | 3/1982 | Zimmerman | 604/174 X |
| 4,344,434 | 8/1982 | Robertson | 604/175 X |
| 4,350,157 | 9/1982 | Hoffa | 604/175 |

FOREIGN PATENT DOCUMENTS 2000684 1/1979 United Kingdom .
2056282 3/1981 United Kingdom .

OTHER PUBLICATIONS

"Reciprocating Peritoneal Dialysis with a Subcutaneous Peritoneal Catheter," Dialysis and Transplantation vol. 7, pp. 834–835 and 838 (Aug. 1978).
Mpls. Medical Research Foundation, Mpls., MN, "Implantable Subcutaneous Blood Access with a Percutaneous, Puncturable Septum," Excerpt from the 11th Annual Contractors' Conference, Jan. 16–18, 1978.
Mpls. Medical Rsearch Foundation, Mpls., MN, "Evaluation of Implantable Subcutaneous Carbon Blood Access Device with Percutaneous Spigot Valve," Excerpt from the 11th Annual Contractors' Conference of Artificial Kidney Program, etc., Jan. 16–18, 1978.
Brochure, "Bentley BioCarbon (R) Vascular Access System," Bentley Laboratories, Inc. (1981).
Proceedings of Seventh Annual Contractors' Conference of the Artificial Kidney Program of the National Institute of Arthritis, Metabolism and Digestive Diseases, pp. 160–161 (1974).
H. Tenckhoff, Chronic Peritoneal Dialysis Manual, FIGS. I–VII.
Brochure, "Pyrolite (R) Carbon Coating for Prosthetic Devices," General Atomic Corp. (1974).

Primary Examiner—C. Fred Rosenbaum
Assistant Examiner—Michelle N. Lester
Attorney, Agent, or Firm—Schroeder, Siegfried, Vidas & Arrett

[57] ABSTRACT

An implantable device for providing communication between interior structures of the body and the exterior of the body, the device comprising a rigid tubular member of biologically compatible material including a transcutaneous stem portion defining a stem cavity therein and a plurality of subcutaneous arm portions in fluid communication with the stem portion. A septum closure in the stem cavity provides an interruptable seal between the stem cavity and each of the arms, permitting the arms to be separately accessed by a cannulae or needle.

7 Claims, 14 Drawing Figures

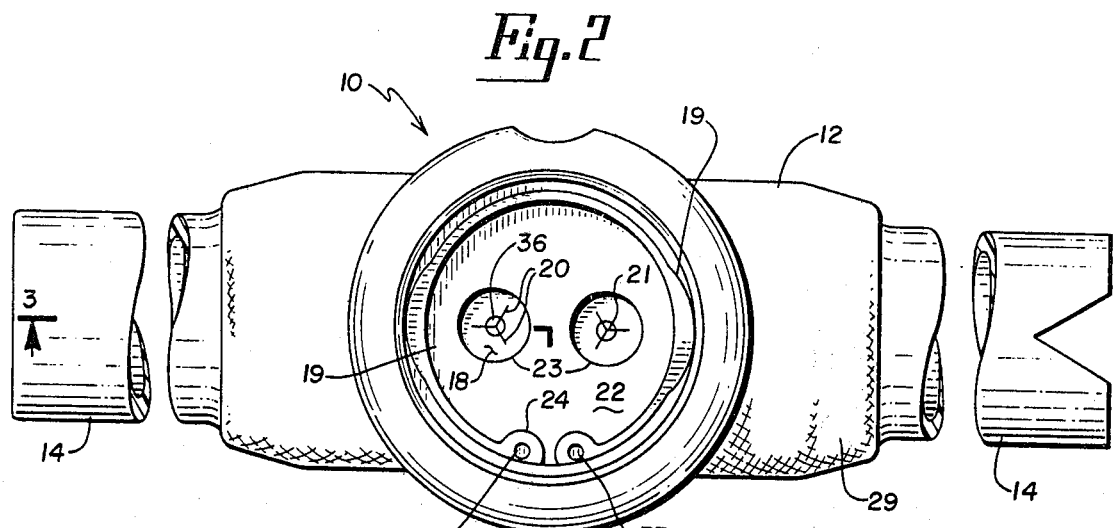
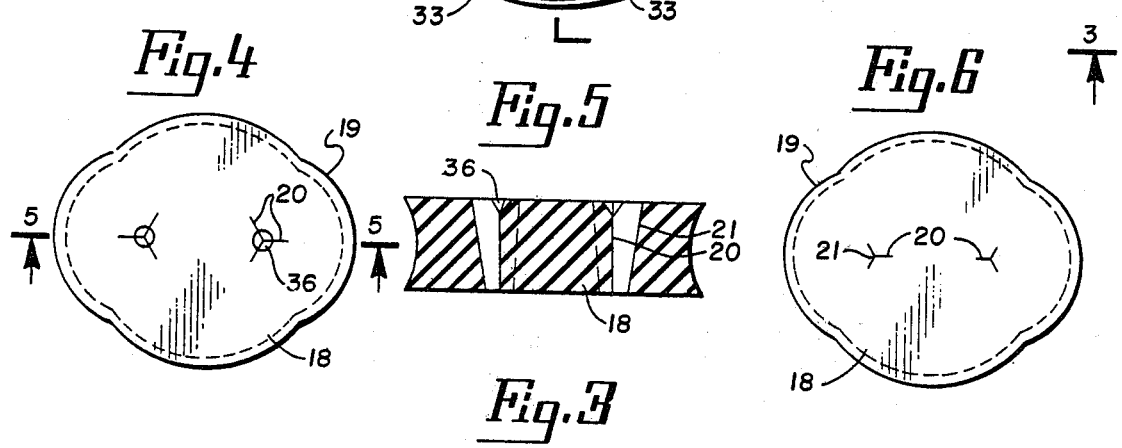
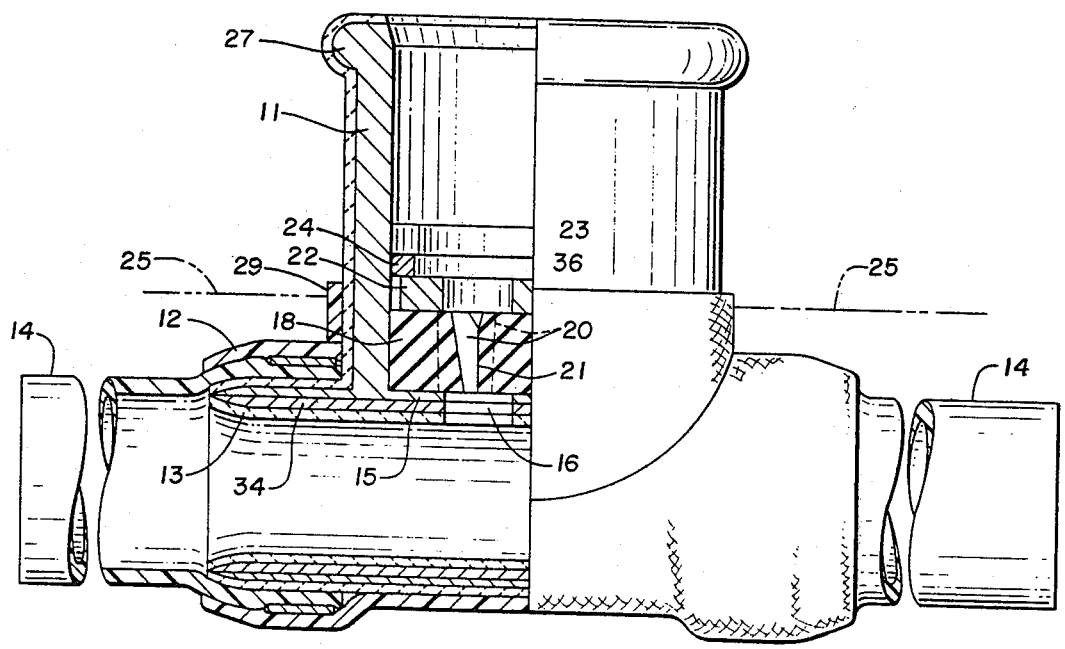

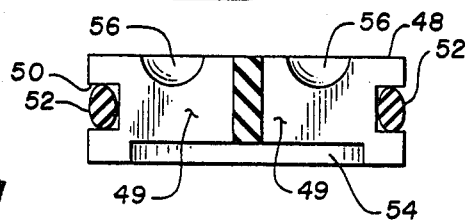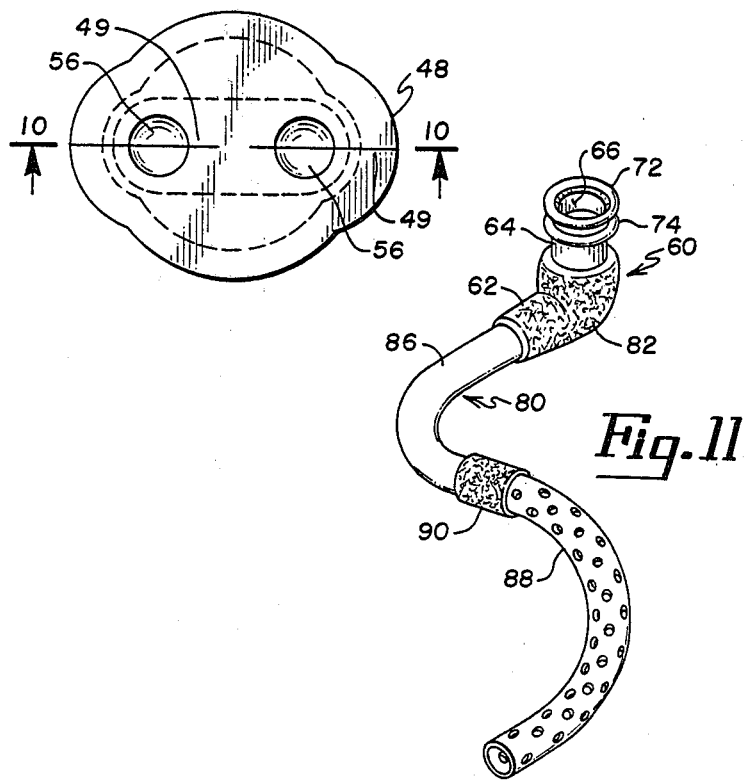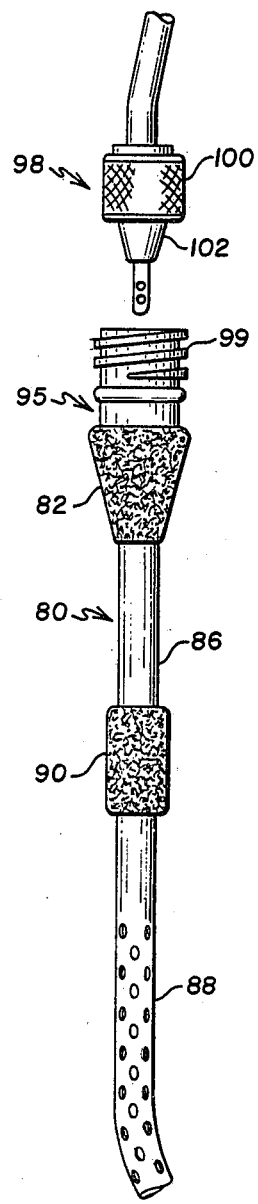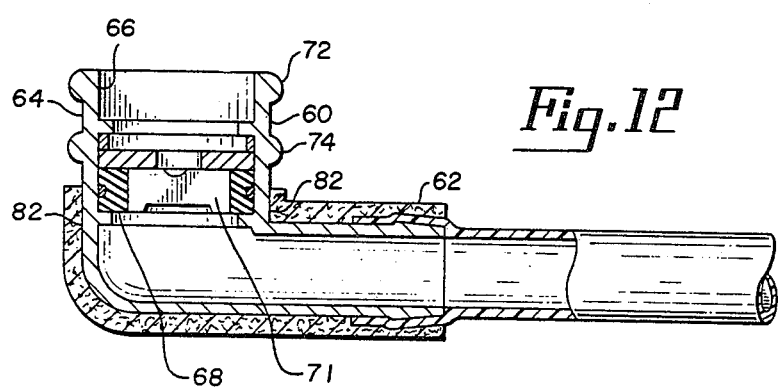

PERCUTANEOUS IMPLANT

DESCRIPTION

BACKGROUND OF THE INVENTION

The present application is directed to implanted devices for providing communication between internal strutures of the body and the exterior of the body. In particular, the application is directed to implantable structures for peritoneal dialysis applications.

Peritoneal dialysis is a process whereby dialysate solution is introduced into the peritoneal cavity for a period of time during which waste materials pass from the blood through the peritoneal membrane into the dialysate. The wastes are removed from the body by drainage of the dialysate from the peritoneal cavity. Peritoneal dialysis may be performed intermittently by machines which automatically fill and drain the peritoneal cavity, usually while the patient is sleeping. Another variation of the process, "continuous ambulatory peritoneal dialysis" (CAPD), has shown increasing use in recent years because, among other reasons, of its relatively low cost and ease of patient self-care and comparison to the more typical hemodialysis treatment. CAPD also allows a patient to engage in most normal life activities while undergoing dialysis. As typically practiced, CAPD utilizes a perforated catheter of a silicon elastomeric material, such as medical grade Dow SILASTIC ™, implanted in the peritoneal cavity and extending through the abdominal wall. Sterile dialysate is infused into the peritoneal cavity by connecting the catheter to a container of dialysate and raising the container above the abdomen so as to the drain the contents into the peritoneal cavity. Prepackaged flexible plastic bags of dialysate offer the advantages that drainage may be accomplished without venting to the atmosphere and that the bag, when empty, may be left connected to the catheter and strapped around the patient's body during residence of the dialysate in the solution. After several hours, the bag is lowered below the abdomen, and the used dialysate fluid permitted to drain back into the bag. The catheter is then connected to a fresh dialysate container which is infused as described into the patient.

In spite of its obvious advantages, CAPD suffers from serious problems because of a frequent occurrence of peritonitis caused by bacterial infection in the peritonium. These infections are most typically caused by nonsterile technique in connecting the catheter to dialysate containers.

Infections may also occur at the exit site where bacteria may invade the body along the exit opening. Subcutaneous cuffs of Dacron ™ (polyethylene terephalate) felt, adhesively joined to the catheter below the skin, have been used to provide tissue ingrowth media so as to achor the tubes and provide a scar tissue barrier to bacterial penetration; but, exit site infections remain a significant problem. This may be related to the flexible nature of the catheter at the exit site, the movement of which may facilitate bacterial penetration. Additionally, dimensional changes in the silicon catheter due to uptake of body fluids or gradual degradation thereof by body fluids may also contribute to the exit site infection problem.

A variety of implantable percutaneous devices have been described for providing external access to internal structures of the body, primarily of the circulatory system. Such structures typically embody flange means for anchoring the device below the skin layer. Porous tissue ingrowth media, such as velour cloth or Dacron felt have also been used with such devices to add to the anchoring ability of the subcutaneous flange members. As described in U.S. Pat. No. 3,783,868, however, such flanged devices exhibit a problem in that epithelium tissue progressively grows down and around the device, eventually encapsulating it and expelling it from the body.

BRIEF DESCRIPTION OF THE INVENTION

In co-pending application Ser. No. 261,719, filing date May 8, 1981 there is described a T-shaped percutaneous device for providing access to the circulatory system. The device is coated with a porous tissue ingrowth media, such as Dacron velour or matte titanium. When implanted, the device becomes securely anchored to the body by tissue ingrowth into the porous material, without the need for a subcutaneous stabilizing flange. The stem of the T extends through the skin layer and is sealed by septum means within the stem through which access may be had to the circulatory system. This device does not have a tendency to be encapsulated by epitheleum tissue and expelled from the body.

It is an object of the present invention to provide a permanently implantable percutaneous device particularly suitable for peritoneal dialysis application on an intermittent basis. Structures of the present invention have improved characteristics for preventing the introduction of bacteria during dialysate changes and for preventing exit site infections.

In accordance with the present invention, there is provided an implantable device for providing communication between interior structures of the body and the exterior of the body, the device comprising a rigid tubular member of biologically compatible material including a transcutaneous stem portion defining a stem cavity therein and a plurality of subcutaneous arm portions in fluid communication with the stem portion. A septum closure in the stem cavity provides an interruptable seal between the stem cavity and each of the arms, permitting the arms to be separately accessed by a cannulae or needle. The device is particularly useful for intermittent peritoneal dialysis applications. The subcutaneous arms are connected to perforated catheters which are placed in different locations in the peritoneum. By using a dual needle assembly to access both arms through the septum, fresh dialysate may be simultaneously pumped into the upper peritoneum while used dialysate is drained from the lower peritoneum.

The subcutaneous exterior portion of the device contains, on at least a part of the exterior surfaces thereof, a porous tissue ingrowth media such as a collar of Dacron velour or a coating of porous titanium.

The percutaneous devices described herein as useful for peritoneal dialysis applications have a longer useful life with reduced risk of exit site infection over conventional silicone elastomer catheter implants. Furthermore, structures of the present invention, which include a septum closure within the tubular body, have the added advantage that the risk of peritonitis is reduced because an added bacterial barrier is provided.

BRIEF DESCRIPTION OF THE DRAWINGS

FIG. 2 is a top plan view of the implantable T-shaped assembly.

FIG. 3 is a side elevational view partly in section as taken along the lines 3—3 of FIG. 2.

FIG. 4 is a plan view top side of the septum.

FIG. 5 is a section view along lines 5—5 of FIG. 4.

FIG. 6 is a plan view of the bottom or interior facing side of the septum.

FIG. 9 is a top plan view of a preferred septum structure.

FIG. 10 is a side section view of the preferred septum taken along line 10—10 of FIG. 9.

FIG. 11 is a pictorial view of an alternate structure of the present invention with peritoneal dialysis catheter attached.

FIG. 12 is a side sectional view of the device of FIG. 11.

FIG. 13 is a front plan view of an alternate peritoneal dialysis structure with a cooperating needle assembly.

DETAILED DESCRIPTION OF THE INVENTION

Blood Access Embodiment

Figure 1:
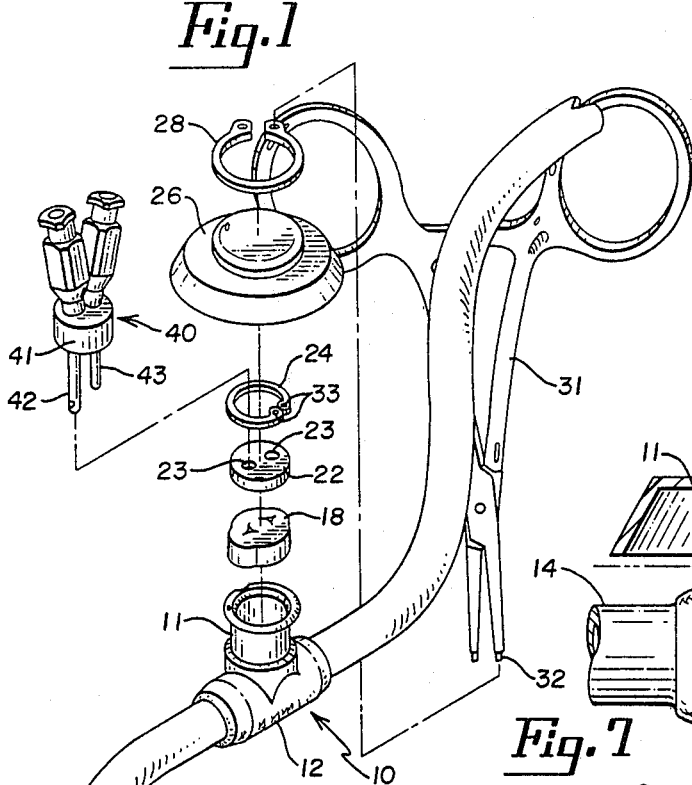
FIG. 1 is an exploded pictorial view of a T-shaped device for use in blood access applications including the implantable portion, a two needle cooperating member and a modified forceps for use in assembly and disassembly of the implanted septum assembly.
Figure 7:
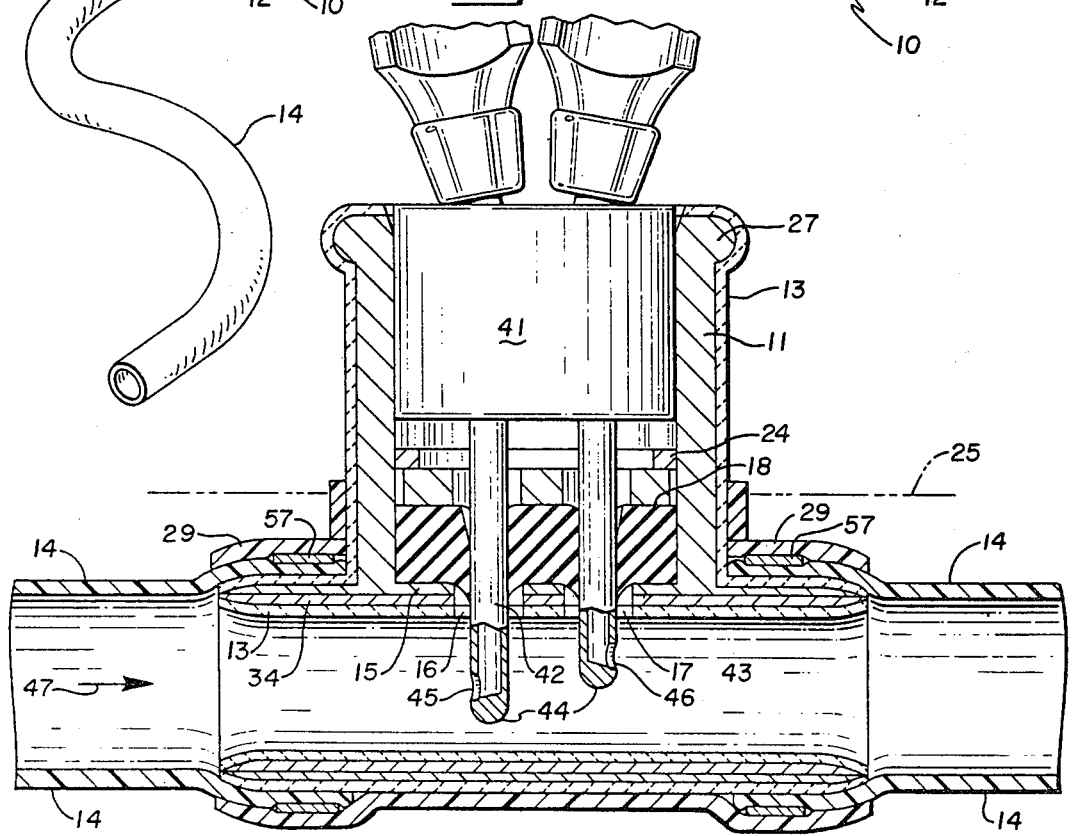
FIG. 7 is a sectional view of a device in accordance with the invention with the cooperating needle assembly in operative engagement with the implantable portion.

Referring to the drawings, there will be seen in FIG. 1 a device in accordance with the invention which includes a T-shaped unitary tubular body generally designated 10 having a stem portion 11 and a straight tube portion 12. Body 10 is formed of a unitary body of a biologically compatible material such as titanium. It is highly advantageous that body 10 be of a unitary construction to eliminate extraneous cavities at points of assembly of non-unitary bodies. At least the external surfaces of body 10 may be coated with a continuous layer of pyrolytic carbon to enhance biocompatability. This is particularly of importance for surfaces that will be blood contacting surfaces, such as the bore when blood is at flow therethrough. Pyrolytic carbon coatings are known to be biologically compatible materials and have been used in implanted structures. See, for example, U.S. Pat. No. 3,783,868. Alternatively, the body 10 may be uncoated titanium or other rigid material. As illustrated in FIG. 7, a snugly fitting sleeve member 34 of graphite may be used to line the interior of tube 12 and underlies coating 13. For coating the interior of a tube, it has been found desirable to have the graphite sleeve to serve as a substrate for the pyrolytic carbon.

Expanded polytetrafluorethylene tubes 14 are shown joined to ends of 12 by slipping over these ends. Dacron (polyethyleneterephthalates) or other body compatible polymeric materials may be used rather than polytetrafluoroethylene. The expanded polytetrafluorethylene slipped over the ends of 12 may be provided as an intermediary for joining blood vessels to the assembly 10. A Teflon shrink band 57 aids in holding the sleeve on. Alternatively, tubes 14 may be attached by nonabsorbable sutures. A suitable expanded polytetrafluorethylene is sold under the trade name Gore-Tex by W. L. Gore Company of Newark, Del. It should be understood that tubes 14 are elective in that it is not necessary that they be present.

Alternatively, an uncoated device 10 may be directly placed in a blood vessel. In such a case, the blood vessel would be slit longitudinally for a sufficient distance for the device 10 to be inserted and the vessel drawn around the device and sutured into place. A collar member 29, as described below, would be used around a portion of the stem to aid in tissue ingrowth to the stem portion.

As can best be seen in FIGS. 3 and 7, body 10 is formed with an internal extension 15 which substantially provides a separation of the internal stem cavity 30 of T-shaped member 11 from the tubular chamber of portion 12, except for the openings 16 and 17. Member 15 provides a support surface for a septum member 18. Member 18 is formed of an elastomer, such as natural rubber, and, as can be seen in FIGS. 2, 4, 5 and 6, has a broadly elliptical configuration. The purpose of this shape is best understood with reference to FIG. 2.

In FIG. 2, there is seen a top view of stem 11. As can be seen, stem 11 has a generally round opening. There is provided an internal shape in the opening along the axis of tube 12 which conforms generally to the ends 19 of the septum 18 for indexing purposes.

As can be seen in FIGS. 2, 4, 5 and 6, septum 18 is pre-cut in a three-directional star or tricuspid form 20. Preferably, although not mandatory, the hole 21 may be completely through septum 18. These cuts facilitate passage of a needle through the septum. At the outer surface of the septum 18, there is a counter sunk region 36 for receiving a needle. The cuts 20 are positioned so that when member 18 is indexed into the opening of T-stem 11, cuts 20 are centered on openings 16 and 17. As a preferred alternative, the needle opening in septum 18 may be actually formed into the septum at the time the septum is fabricated. When the septum is pressed into place, the compression will seal the openings 21.

Overlying septum 18 is a pressure plate 22 of titanium or the like which defines openings 23 which are spaced to conform in position to slits 20 and openings 16 and 17. Pressure plate 22 is, in turn, locked into engagement with septum 18 by a spring retaining ring 24.

FIG. 9 and 10 show a peritoneal septum configuration. The preferred septum 48, which is more fully described in co-pending application Ser. No. 209,058, filing date Nov. 21, 1980 has, as preformed needle openings, two slits 49 cut through the septum and extending from near the center of the septum out to the edge thereof.

The edges of septum 48 have a groove 50 therein encircling the entire body thereof. Groove 50 carries an elastomeric ring 52 which preferably has an elliptical or circular cross-section. Ring 52, which has a smaller inner circumference than that of the septum, services to hold the slit septum together and maintain the slit surfaces together in sealed relationship by applying an inwardly directed radial force on septum 48. The elliptical or circular shape of the ring leaves gaps in the groove into which septum material may move as the needle is inserted.

The septum is also preferably provided with an elongated bottom recess 54 and a pair of generally semispherical top recesses 56 aligned with holes 23 in pressure plate 22 when assembled in the device stem.

Figure 8:
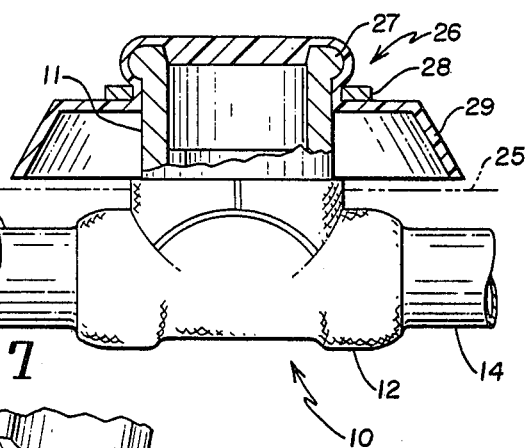
FIG. 8 is a side elevational view partly in section of the T-shaped implantable structure and cover assembly.

A cap member 26 snaps over a flanged edge 27 as seen in FIG. 8 ad is held in sealed relationship therewith by a retaining ring 28. The lower flared edge 70 of cap 26 will be spaced, in use, slightly above the skin 25 of the user. Pressure contact with the skin of flared edge 70 is undesirable as necrosis may occur. Overall, there is provided a profile for the exposed external portion of member 10 that is less likely to catch an object, such as clothing. Cap 26 also provides a means whereby an antiseptic, such as Betadine (iodine polyvinylpyrolidone complex) may be included in cavity 30 to maintain the unit sterile between usage.

The assembly described above is implantable in the patient by surgical techniques that are known and form no part of the invention. It is desirable to have the amount of the stem protruding above the skin line at a minimum amount compatible with permitting a cap member seal. Implantation may be in various manners and modes, including, but not limited to, the following: by anastomosis to 14, i.e. by splicing the ends of a blood vessel to opposite ends of assembly 10. Assembly 10 may be positioned into a blood vessel that has been longitudinally slit for a distance sufficient to permit insertion of the device. In this latter case, the blood vessel is sutured about the device to form a seal and the sleeves 14 are not used.

To aid in accomplishing tissue growth onto the portion of the stem 11 below the skin lines 25, a collar member 29 of porous plastic material, such as polyethylene terephthalate, sold by E. I. Dupont under the trademark Dacron, may be used. The portion of stem 11 above the dermis region is uncoated to reduce the risk of infection occurring by bacteria making their way down along the collar 29. If the external surface of stem 11 is titanium, the titanium may have a matte surface in the region of collar 29 and, thus, eliminate need of collar 29.

When access is to be made to the blood system, the cap 26 is removed. The interior cavity region 30 thus exposed can be rinsed with appropriate sterilizing agents that are removed prior to insertion of a needle through openings 23, 20 and 16. It is preferred that cavity 30 be filled with and hold a sterilizing solution, such as described previously, between usage. This sterilizing solution can be placed in cavity 30 before closing with cap 26 or a hypodermic may be used to inject the solution through the cap. Desirably, the needle used to penetrate the septum will have a closed rounded end with one or more openings 45, 46 at the side thereof. A blood sample can be drawn or material such as drugs inserted through the needle, as desired.

The device described can be implanted into a patient and remain essentially permanently. However, if a need arises to replace the septum 18 after prolonged use, this can readily be done without need of surgical procedures. A modified forceps 31 is machined or ground to provide tips 32 of a size to be positioned into holes or recesses 33 in retaining ring 24. The ring may be withdrawn along with pressure plate 22 and septum 18 for cleaning and/or replacement. Of course, steps should be taken to block the body blood pressure so as to prevent appreciable blood flow outwardly through openings 16 and 17 during the assembly or disassembly.

It is desirable to utilize a cooperating assembly, such as a member 40. Even when a simple needle is on a standard syringe, it is desirable that the needle have a rounded end as will be described below. Member 40 is constructed of a cylindrical block of metal 41 through which two hollow needle members 42 and 43 extend in sealed relationship to member 41. These needle members are positioned so as to index with openings 23 in pressure plate 22. As can best be seen in FIG. 7, the needles have rounded closed ends 44 and each have at least one side opening 45 and 46, respectively. As shown, the needle is solid (cavityless) below the lower edge of openings 45 and 46. This construction is highly advantageous. The rounded closed end readily passes through septum 18 with a reduced tendency to cut and break pieces of a septum as a result of passage therethrough over use of a conventional hypodermic needle. The solid lower end avoids the presence of entrapped air. One can also position the openings in the needles so that if blood flow is in the direction shown by arrow 47, the needle opening 45 is directional to withdrawal of blood, while opening 46 is directional to return of blood. The top of the needle can be joined to any suitable construction to be connectable to external blood flow tubing or other types of apparatus.

An alternate needle assembly structure, as well as other improvements in the blood access embodiment of the present invention, are disclosed in co-pending application Ser. No. 209,058, filed Nov. 21, 1980, and assigned to the assignee of the present invention. The disclosure of application Ser. No. 209,058 is incorporated herein by reference.

Peritoneal Dialysis Embodiments

FIGS. 11-14 show alternate embodiments of the invention which are especially applicable to peritoneal dialysis applications. As with the T-shaped blood access device described previously, the devices of FIGS. 11-14 comprise a flangeless tubular body having a smooth upper exterior surface and a lower, subcutaneous surface which carries a layer of porous tissue ingrowth media, such as a collar or cuff of Dacron velour cloth or felt. The peritoneal dialysis structures will preferably include a septum seal means within the interior of the tubular body as does the T-shaped blood access device described above.

The device in FIGS. 11 and 12, generally designated by the numeral 60, is substantially identical to that of the T-shaped device described above, with the exception that it has an L-shape in only one subcutaneous connector arm 62. Device 60 includes a stem portion 64 and an interior cavity portion 66 including a septum closure 68 held in place as described above. Septum 68 is modified from that shown in FIGS. 9 and 10 in that the needle opening slits 71 is centrally located and does not extend to the edges of the septum. This configuration is designed to accommodate a single needle.

Also, as with the T-shaped device described previously, implant 60 includes a flanged upper edge 72 which can carry a cap member. A second excutaneous flange 74 may also be provided on the outer surface of the device. Second flange 74 provides means whereby the stem may be held by a clamping tool during needle insertion or removal or septum change operations.

As shown in FIG. 11, the inventive device, as implanted, will include a silicone catheter member 80 attached to arm 62. The porous Dacron collar 82 extends over the joint between catheter 80 and device 60.

As is conventional with percutaneous catheter implants, catheter 80 will preferably have a forward, unperforated portion 86 which will be implanted so as to lie in the abdominal tissue between the skin and the peritoneal wall.

The lower portion 88 of catheter 80 is perforated, the perforations beginning about half the length below the point where the catheter enters the peritoneal cavity.

Also, as typical with percutaneous catheters, catheter 80 will preferably include a second cuff 90 adhesively affixed thereto on the unperforated portion, somewhat above the entry point of the catheter into the peritoneal cavity. This second cuff serves to anchor the catheter against significant movement about the peritoneal entry point which could cause damage to the peritoneal wall.

Because the structures for peritoneal dialysis do not carry pressurized liquids, as is the case for the blood access embodiment described above, it is not imperative that the septum seal means be employed in the device of the present invention. As with percutaneous silicone catheter implants, the devices of the present invention may simply be capped to keep out bacteria and other contaminants when not in use. A straight tube device 95 of this type is shown in FIG. 13 with a cooperating needle structure 98. Device 95 includes a threaded excutaneous portion 99 onto which cap 100 of the needle assembly 98 may be screwed. Rather than include a septum and retaining means within its stem, the interior configuration of device 95 is tapered to mate with a tapered male Leur portion 102 on the needle assembly. The same device as shown in FIG. 13 may also be equipped with a septum and retaining means within its stem.

The use of a septum closure in the inventive structure is preferred because they provide added advantages in providing against peritonitis because the septum seal provides an additional bacterial barrier. As previously described, the cavity above the septum can be filled with antiseptic solution, such as Betadine TM, so as to provide a much more effective bacterial barrier than can be accomplished by a simple cap or a swabbing of the interior connector surfaces with an antiseptic solution between uses.

Figure 14:
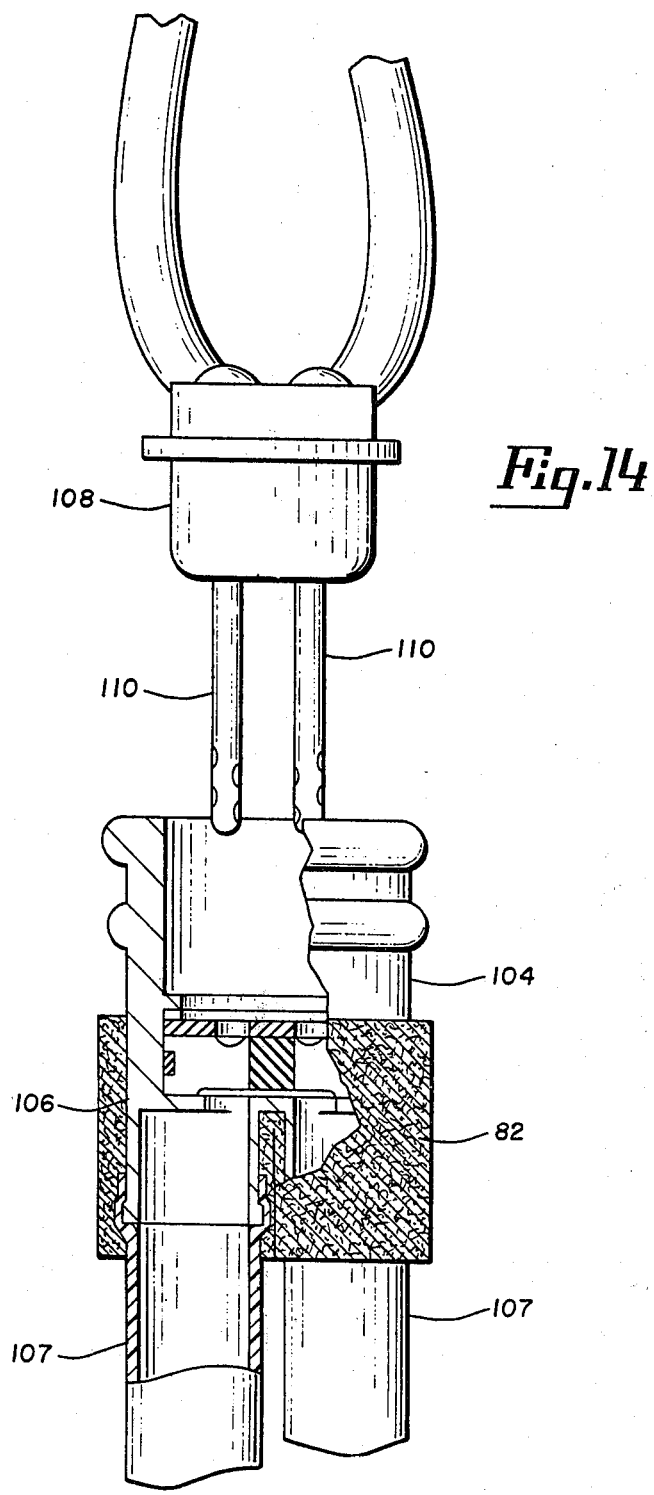
FIG. 14 is a front plan view of another alternate peritoneal dialysis structure with a cooperating needle assembly, which is the subject of this application.

FIG. 14 shows a Y-shaped, two channel percutaneous device in accordance with the present invention, useful in intermittent automatic peritoneal dialysis. The specific embodiment of FIG. 14 is the co-invention of Louis C. Cosentino and Felix J. Martinez. As with the T-shaped device 10 and L-shaped device 60 described above, device 104 include a septum closure within the stem cavity. Device 104, however, includes two downwardly extending outlet arms 106, each of which is connected to a catheter member 107. A cooperating needle assembly 108 carries a pair of needles 110 which extend through the septum and down into the interior of tubular arms 106. The two catheters 107 are placed in different portions of the peritoneal cavity. Dialysate may be pumped into the peritoneal cavity via one of needles 110 and catheters 107 and simultaneously used dialysate may be removed via the other catheter/needle combination. Preferably, the inflow catheter will be placed above the outflow catheter so that the used dialysate may be drained without suction by gravity.

Arms 106 of device 104 extend downwardly so that needles 110 may be extended therein to prevent mixing of fresh and used dialysate. Alternatively, a T-shaped device similar to device 10 may be used if an intermediate central barrier and tube portion 12 is included so as to divide tube portion 12 into two separate chambers, one for filling and the other for draining the dialysate.

Also, as with the blood access device, the devices of the present application useful for peritoneal dialysis applications will preferably be made of titanium and, still more preferably, will contain an at least several angstrom layer of pyrolytic or vapor deposited carbon.

What is claimed is:

1. A percutaneous device for providing communication between the body exterior and the body interior, the device comprising:
   a rigid tubular body of biologically compatible material, said body including a transcutaneous stem portion defining a stem cavity therein and a plurality of subcutaneous arm portions joined to and in fluid communication with said stem cavity, said stem having a substantially constant outer diameter along its subcutaneous portion and to at least the excutaneous portion of the stem, an elastomeric septum within said stem cavity, and means within said stem cavity for holding said septum member in a fixed relationship to said arms so as to provide a separate interruptable seal between each of said arms and said stem cavity, and said device including a porous tissue ingrowth media on at least a part of the exterior subcutaneous surfaces of the device and wherein said ingrowth media is limited to said subcutaneous surfaces.

2. A device as in claim 1 wherein the biologically compatible material is titanium.

3. A device as in claim 2 wherein the titanium surfaces are coated with vapor deposited carbon.

4. A device as in claim 1 wherein the tissue ingrowth media is a porous collar of polyethyleneterephthalate.

5. A device as in claim 1 further comprising a plurality of flexible tubular catheter members, each in engagement with one of said arms and wherein said tissue ingrowth media extends over the joint between said arm and said catheter members.

6. A device as in claim 5 wherein each said catheter member includes a portion thereof having a plurality of perforations through the sides thereof.

7. A device as in claim 1 including two said arm portions each extending downwardly from said stem portion in a generally Y-shaped configuration.

* * * * *